(12) United States Patent
Paul et al.

(10) Patent No.: US 6,492,546 B2
(45) Date of Patent: Dec. 10, 2002

(54) PROCESS FOR PREPARING UNSATURATED CARBOXYLIC ESTERS

(75) Inventors: Jean-Michel Paul, Metz (FR); Patrick Busca, Bening les Saint-Avold (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 10/025,988

(22) Filed: Dec. 26, 2001

(65) Prior Publication Data

US 2002/0133041 A1 Sep. 19, 2002

(30) Foreign Application Priority Data

Dec. 26, 2000 (FR) .............................................. 00 17023

(51) Int. Cl.[7] .......................... C07C 69/52; C07C 69/00
(52) U.S. Cl. ........................................ 560/205; 560/129
(58) Field of Search ................................ 560/205, 129

(56) References Cited

U.S. PATENT DOCUMENTS 3,776,947 A   12/1973  Noboru Shimizu et al.
5,645,696 A  *  7/1997  Woo et al.

FOREIGN PATENT DOCUMENTS

FR          2186457          1/1974

* cited by examiner

Primary Examiner—Alan L. Rotman
Assistant Examiner—Héctor M Reyes
(74) Attorney, Agent, or Firm—Millen, White, Zelano & Branigan, P.C.

(57) ABSTRACT

This process for preparing an unsaturated carboxylic ester by esterifying an unsaturated carboxylic acid with an alcohol in the presence of a cationic resin catalyst, the water of reaction being removed in the form of an azeotrope with the esterifying alcohol or with a solvent, is characterized in that the esterification reaction is conducted by passing the mixture of reactants in upflow mode through a bed (9) of the said cationic resin in a recirculation loop (2) which is combined with a stirred tank (1) in which the reactants are mixed and from which the water of reaction is removed azeotropically.

20 Claims, 1 Drawing Sheet

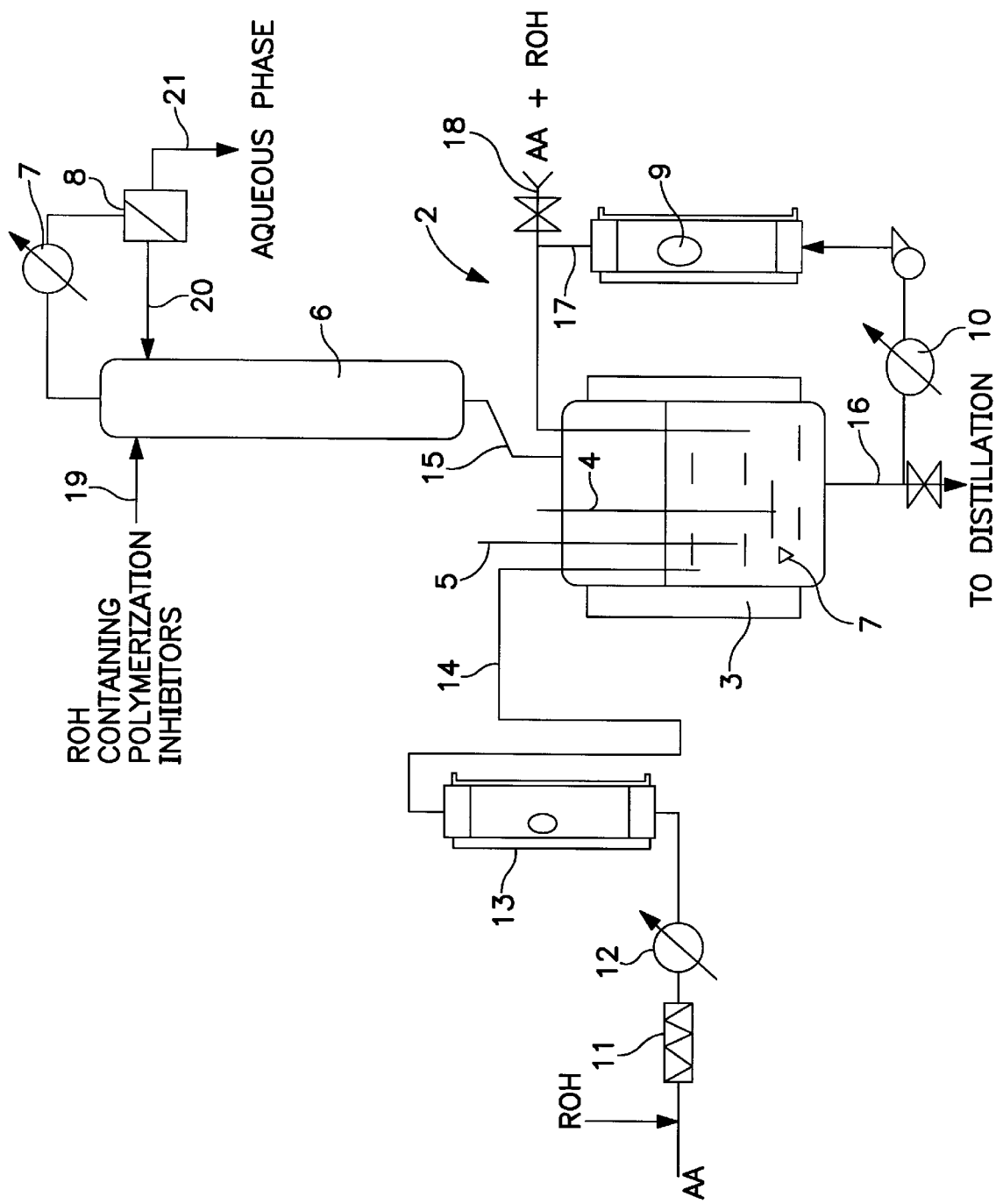

PROCESS FOR PREPARING UNSATURATED CARBOXYLIC ESTERS

The present invention relates to an improved process for preparing unsaturated carboxylic esters.

A number of processes have been described in the literature for the synthesis of unsaturated carboxylic esters.

The catalysts generally used are acids of the sulphuric acid, para-toluenesulphonic acid, methanesulphonic acid or similar type. The water of reaction is removed in the form of an azeotrope with the esterifying alcohol or with a solvent such as cyclohexane, toluene, etc.

The use of these catalysts results in the formation of by-products and necessitates the use of appropriate materials which are resistant to corrosion, especially with sulphuric acid. The residual acid is then neutralized. The neutralizing operations/washings are laborious and polluting.

The use of strong cationic resins of sulphonic type which do not exhibit these disadvantages is widely described in the literature, in connection with esterification.

The American patent U.S. Pat. No. 4,833,267 describes the synthesis of $C_1$–$C_2$ (meth)acrylic esters in a continuous regime in a stirred reactor with the aid of a mechanical stirrer operating at a power of from 0.05 to 2 kW/m$^3$. The cationic resin is held in suspension in the reaction medium. The drawback of this technique is the mechanical stress to which the resin is subjected, resulting in the said resin becoming fragile and breaking, with a drop in catalytic activity.

The Japanese patent application JP-A-58 192 851 describes the use of a resin-filled, jacket-heated tubular catalytic reactor topped with a distillation column for removing the water of reaction. A drawback of this technique is the prolonged contact of the water with the reactants and products, thereby bringing about the formation of heavy by-products, to the detriment of the selectivity.

The American patent U.S. Pat. No. 5,645,696 describes the use of a top-fed multistage catalyst bed for the synthesis of unsaturated carboxylic esters. The reactor is composed of from 1 to 10 resin stages and is topped by a distillation column in which the water of reaction is removed. Water is evaporated with the aid of an external exchanger. The principal drawback of this system is its laboriousness and the risks of blockage of the plates by polymers.

In accordance with the present invention, a proposal is made for an enhanced process for continuously synthesizing esters of unsaturated carboxylic acids by esterifying resins of aliphatic alcohols, which overcomes the drawbacks of the processes claimed in the American patents U.S. Pat. No. 4,833,267 (breakage of resins under the effect of mechanical stirring) and U.S. Pat. No. 5,645,696 (complexity of the reaction zone, consisting of a multistage bed, with risk of fouling by polymers) and in the Japanese application JP-A-58 192 851.

According to the present invention, by combining m a first fixed bed of resin, fed from the bottom, with a If reactor consisting of a blending tank provided with a recirculation system at the bottom through a resin cartridge, high conversion rates are obtained in combination with equally high selectivities, thereby simplifying the downstream purifying operations. Moreover, the resin charging/discharging operations are extremely simple.

The present invention accordingly provides a process for preparing an unsaturated carboxylic ester by esterifying an unsaturated carboxylic acid with an alcohol in the presence of a cationic resin catalyst, the water of reaction being removed in the form of an azeotrope with the esterifying alcohol or with a solvent, characterized in that the esterification reaction is conducted by passing the mixture of reactants in upflow mode through a bed of the said cationic resin in a recirculation loop which is combined with a stirred tank in which the reactants are blended and from which the water of reaction is removed azeotropically.

Passage over the resin takes place in the upward direction so as to keep the resin in suspension and to facilitate the thermal exchanges.

In accordance with one advantageous embodiment of the present invention, a partial reaction is conducted upstream of the stirred tank by passing the mixture of reactants in upflow mode through a second bed of the cationic resin catalyst.

The unsaturated carboxylic acid employed is advantageously acrylic or methacrylic acid. As for the alcohol employed it is, preferably, a primary or secondary aliphatic alcohol, in particular a $C_1$–$C_{12}$ alcohol, such as, in particular, n-butanol, 2-ethylhexanol and n-octanol.

The overall unsaturated carboxylic acid/alcohol molar ratio is generally between 0.6 and 1, preferably between 0.7 and 0.9.

The reaction is generally conducted in the presence of at least one polymerization inhibitor selected in particular from phenothiazine, hydroquinone, hydroquinone monomethyl ether, and sterically hindered phenols, such as 2,6-di-tert-butyl-para-cresol, at levels in the medium of between 500 and 5000 ppm. Bubbling of air is generally carried out within the blending tank in order to reinforce the action of the polymerization inhibitor or inhibitors. The latter are generally introduced with the reactants at the top of the distillation column surmounting the stirred tank.

In accordance with one particular embodiment of the process of the invention, a portion of the alcohol is introduced at the top of the distillation column surmounting the stirred tank, one or more polymerization inhibitors being advantageously combined with the alcohol introduced at the top of the column, and the mass fraction of the alcohol thus introduced at the top of the column in relation to the alcohol introduced in the tank 1 being from 20 to 60%, preferably from 30 to 50%.

The temperature at the top of the bed of resin is generally between 70 and 100° C., more particularly between 80 and 95° C. (above 100° C., thermal degradation of the resins is observed); the temperature of the blending tank is generally between 100 and 110° C., with the reaction mixture exiting the blending tank being cooled to 80–90° C. then recirculated through the bed of resin.

The cationic resin is advantageously a strong cationic styrene/divinylbenzene resin containing sulphonic groups and having an ionic capacity of between 0.5 and 2.2 equivalents/liter. By way of examples of resins, mention may be made of that sold under the name DIAION® PK 208 by the MITSUBISHI CHEM. Company and those sold under the names XE 586, XE 386 and AMBERLIST 39 by the ROHM & HAAS Company.

Generally, the reaction mixture is circulated through the (first) bed of resin, the overall residence time on the (first) bed of resin being generally between 0.5 and 2 h.

The water generated by the esterification is distilled off in the form of an azeotrope. It is possible, as already indicated, to use an aliphatic or aromatic solvent which forms an azeotrope with water, such as cyclohexane, heptane, toluene, etc. As a general rule, however, it is the alcohol itself which plays this part.

The vapours which distil in the column contain, besides the water, the esterifying alcohol, the carboxylic ester and the carboxylic acid. A return flow of alcohol J containing from 500 to 1000 ppm of inhibitors as described above makes it possible to limit the ascent of acid at the top and the losses via the aqueous decantation phase.

The vapours condensed at the top of the column are decanted at ambient temperature:

the organic phase is returned to the distillation column, with its octene concentration being regularly lowered; and the aqueous phase is removed.

The working pressure at the top of the distillation column surmounting the stirred tank is generally from $9.33 \times 10^3$ to $5.3 \times 10^4$ Pa (from 70 to 400 mmHg).

In the abovementioned preferred embodiment in which a first resin stage is sited upstream, the temperature at the top of the second bed is generally from 80 to 95° C. and the reactor containing the second bed is operated at atmospheric pressure under conditions of thermodynamic equilibrium; the residence time on the resin of the second bed is generally from 20 to 60 minutes. Moreover, at the input to the second catalytic bed, the acid/alcohol molar ratio is generally top-heavy in acid.

The examples which follow illustrate the present invention without, however, limiting its scope. In these examples, the percentages are by weight unless indicated otherwise and the following abbreviations have been used:

AA : acrylic acid
HQ : hydroquinone
HQME : hydroquinone monomethyl ether
BuOH : butanol
E2HOH : 2-ethylhexanol
ABu : butyl acrylate
A2EH : 2-ethylhexyl acrylate

BRIEF DESCRIPTION OF THE DRAWING

The attached FIGURE is a schematic flowsheet of a preferred embodiment of the invention.

DETAILED DESCRIPTION OF THE DRAWING

The apparatus shown in the single FIGURE of the attached drawing comprises a blending tank 1 with which an external circulation loop 2 is combined.

The blending tank 1 is heated by a jacket 3 fed with a heat transfer fluid. It is stirred mechanically with the aid of a stirrer means 4. Bubbling of air, required for the stabilization of the reaction medium in the tank 1, is carried out via an introduction pipe 5.

The tank 1 is topped with a packed distillation column 6 with a top-mounted condenser 7, decanter 8, receiver and trap. The level of the interface in the decanter is regulated by means of a high-impedance detection probe.

Sited on the circulation loop 2 is a reactor 9, with a jacket fed with a heat transfer fluid and with a resin packing (first cartridge 9), and a heat exchanger 10 intended for lowering the temperature of the reaction stream before it passes over the resin located within the cartridge 9. The reactants in the cartridge 9 are circulated in the upward direction so as to hold the resin in suspension in the liquid and thereby to promote exchanges of matter and of heat.

The tank 1 is fed with the mixture of reactants: acrylic acid and alcohol; the mixing operation is carried out in the static mixer 11. A preheater 12, intended to bring the reactants to the desired temperature, is sited at the exit of the static mixer 11.

In one preferred configuration, as illustrated in the FIGURE, a reactor 13, with a jacket fed with a heat transfer fluid and with a resin packing (second cartridge 13), is sited upstream of the tank 1. The reaction mixture circulates therein in the upward direction and the resin is held in suspension in the liquid. This tubular catalytic reactor 13, which operates under conditions of thermodynamic equilibrium, is in fact a first reaction stage which carries out part of the conversion of the reactants before they reach the second, finishing stage, which operates by shifting the equilibrium.

The mixture of reactants 14, preheated in 12 and having undergone partial conversion in the reactor 13, is supplied to the blending tank 1. The water of reaction is removed from the tank 1 in the form of an azeotrope 15. The crude reaction product 16 at the exit of the tank 1 is divided into a part which is directed to the distillation and a part which is directed to the resin cartridge 9. At the exit from the cartridge 9, the crude reaction product 17 is returned to the blending tank 1.

The reactants may also be introduced directly at 18 into the circulation loop 2.

Furthermore, a feed pipe 19 at the top of column 6 makes it possible to supply this column with the alcohol, which contains polymerization inhibitors.

The decanter 8 at the top of column 6 allows separation into an organic phase 20, which is returned in a flow to the column 6, and an aqueous phase 21, which is removed.

The resins used in the examples are as follows:

Resin 1: Resin sold by the ROHM & HAAS Company under the name XE 586; its characteristics are as follows:
  ionic capacity: 0.5 eq/l;
  mean diameter: 0.53 mm.
Resin 2: Resin sold by the MITSUBISHI CHEM. Company under the name DIAION PK 208.

EXAMPLE 1

Preparation of Butyl Acrylate

The apparatus used in this example is that described with reference to the single FIGURE of the attached drawing, except that the blending tank 1 is not preceded by the jacketed resin cartridge 13. The thermostated, jacketed tank 1 is made of stainless steel and has a useful volume of 700 ml. The jacket 3 is fed with oil at 130° C. The stirrer 4 is of the anchor type. The packed column 6 has an internal diameter of 22.5 mm and a decanter with a volume of 50 ml.

The catalytic reactor 9 consists of a stainless steel tube with a jacket fed with oil at 130° C.; its internal diameter is 30 mm and its height is 600 mm. It contains 134 g of Resin 1, dried in a ventilated oven beforehand.

The assembly may operate under subatmospheric pressure.

The reactants, AA (+inhibitors) and BuOH, are fed in an AA/BuOH molar ratio of 0.77/1 at a flow rate of 270 ml/h into the tank 1. The aforementioned inhibitors consist of 500 ppm of 1,1,3-tris(2-methyl-4-hydroxy-5-tertbutylphenyl)butane (TOPANOL® CA from the SEAL SANDS CHEMICALS Company) and 500 ppm of HQ in relation to the AA. The temperature in the tank 1 is 100° C. and that at the centre of the bed of resin 9 is 92° C. The crude reaction product 16 is recirculated via the base of the tank 1 by means of a centrifugal pump at a flow rate of 4 l/h over the bed of resin 9. The refresh rate of the reactor 1 is approximately 10 times/h.

The operating pressure is $3.95 \times 10^4$ Pa (300 mmHg), and the temperature at the top of the column 6 is 75–76° C. The water of reaction is distilled off in the form of an azeotrope with BuOH.

The flow rate of the aqueous phase 21 is 23 ml/h, with the composition by mass of the said aqueous phase being:

| | |
|---|---|
| Water | 9.3% |
| BuOH | 6.9% |
| AA | 200 ppm. |

The outgoing flow rate of the crude reaction product is 246 ml/h, with its composition by mass being:

| | | |
|---|---|---|
| BuOH | 19.3% | |
| AA | 5.8% | |
| Water | 0.25% | |
| ABu | 72.4% | |
| Butyl acetate | 84 | ppm |
| Butyl ether | 2000 | ppm |
| Butyl propionate | 257 | ppm |
| Butyl hydroxypropionate | 352 | ppm |
| Butyl butoxypropionate | 900 | ppm. |

The degree of conversion of the AA is 87%; the selectivity in relation to AA consumed is 99.2%.

EXAMPLE 2

Preparation of 2-ethylhexyl Acrylate

The apparatus and resin used were the same as in Example 1.

A mixture of AA (81 g/h) and E2HOH (64 g/h) containing 500 ppm of 1,1,3-tris(2-methyl-4-hydroxy-5-tert-butylphenyl)butane (TOPANOL® CA) and 500 ppm of HQ calculated relative to the overall charge of AA+E2HOH, is introduced continuously into the blending tank 1. The temperature in the tank 1 is 99° C.

A complement of E2HOH containing 500 ppm of HQ is added at the top of column 6 (96 g/h) so as to prevent the ascent of AA. The overall AA/E2HOH molar ratio is therefore 0.91/1.

The reaction mixture is recirculated at a flow rate of 36 l/h in the resin cartridge 9. The temperature at the centre of the bed of resin 9 is 95° C.

The water of reaction is removed in the form of a water/E2HOH azeotrope additionally containing AA and A2EH.

The vapours are condensed at the top and decanted at ambient temperature.

The pressure at the top is 1.86×10⁴ Pa (140 mmHg).

The aqueous decantation phase is withdrawn at a flow rate of 12.4 g/h. It contains 96% water and 3.7% E2HOH.

The organic phase has the following composition by mass:

| | | |
|---|---|---|
| AA | 3% | |
| E2HOH | 95.7% | |
| A2EH | 0.4% | |
| Octenes | 830 | ppm |

The crude reaction product is withdrawn continuously at a flow rate of 226 g/h. Its composition by mass is as follows:

| | | |
|---|---|---|
| E2HOH | 26% | |
| AA | 10.8% | |
| Water | 0.9% | |
| A2EH | 60.5% | |
| Octenes | 450 | ppm |
| Dioctyl ether | 900 | ppm |
| 2-ethylhexyl hydroxypropionate | 770 | ppm |
| 2-Ethylhexyl acryloyloxypropionate | 500 | ppm |
| 2-Ethylhexyl 2-ethylhexyloxypropionate | 650 | ppm. |

The degree of conversion of the AA is 69.4%; the selectivity with respect to AA consumed is 94.5%; and the selectivity with respect to E2HOH consumed is 97%.

EXAMPLE, 3

Preparation of 2-ethylhexyl Acrylate

The apparatus of Example 1 is used, preceded by the tubular reactor 13 described with reference to the single FIGURE of the attached drawing.

The reactor 13 is a tubular reactor with a jacket in stainless steel which is fed with oil at 130° C. It contains 134 g of Resin 1, dried in a ventilated oven.

The reactants, AA containing polymerization inhibitors (500 ppm of 1,1,3-tris(2-methyl-4-hydroxy-5-tert-butylphenyl)butane (TOPANOL® CA) and 500 ppm of HQ) and E2HOH, are mixed and preheated to 90° C. then introduced at the base of the catalytic reactor 13 by a pump at a flow rate of 615 ml/h. The initial AA/E2HOH molar ratio is 1.26.

The temperature of entry into the cartridge 13 is 90° C. The temperature of exit from the cartridge 13 is 95° C. The reaction is carried out without a shift in equilibrium. The direction of passage of the reactants over the resin is upward. The residence time on the resin is 36 min.

The composition by mass of the crude product of the exit from the cartridge 13 is as follows:

| | | |
|---|---|---|
| E2HOH | 29.6% | |
| AA | 24.7% | |
| Water | 4.4% | |
| A2EH | 41.2% | |
| Octenes | 320 | ppm |
| Maleic impurities (maleic acid + mono- + dimaleates) | 1300 | ppm |
| 2-Ethylhexyl hydroxypropionate | 0.25% | |
| 2-Ethylhexyl acryloyloxypropionate | 0.3% | |
| 2-Ethylhexyl 2-ethylhexyloxypropionate | 0.2%. | |

The degree of conversion of the AA is 51.2% (approximately 98.5% of the thermodynamic equilibrium).

The crude product exiting the cartridge 13 is stored in an intermediate vessel and then pumped into the reactor 1.

The reaction mixture is introduced at a flow rate of 188.1 g/h into the blending tank 1.

A complement of E2HOH (63 g/h) containing 500 ppm of HQ is added at the top of the column, thereby bringing the overall (first+second stage) AA/E2HOH molar ratio to 0.8/1.

A gentle bubbling of air is introduced into the blending tank 1. The jacket of the tank is fed with oil at 150° C. The temperature in the tank 1 is 104–105° C. The temperature at the centre of the cartridge of resin is 95° C. The pressure at the top of the column is 6.66×10³ Pa (50 mmHg). The recirculation flow rate is 30 l/h.

The crude product at the exit from the second stage (233.8 g/h) has the following composition by mass:

| | |
|---|---|
| E2HOH | 27.5% |
| AA | 6.8% |
| Water | 0.14% |
| A2EH | 63.5% |
| Octenes | 110 ppm |
| Ethers | 550 ppm |
| Maleic impurities (maleic acid + mono- + dimaleates) | 1500 ppm |
| AA dimer | 250 ppm |
| 2-Ethylhexyl hydroxypropionate | 0.3% |
| 2-ethylhexyl acryloyloxy-propionate | 0.8% |
| 2-Ethylhexyl 2-ethylhexyloxy-propionate | 0.9%. |

The overall degree of conversion of AA is 79%. The selectivity with respect to AA consumed is 96%. The selectivity with respect to E2HOH consumed is 98.7%.

The water of reaction is removed continuously in the form of a water/E2HOH azeotrope additionally containing octenes, AA and A2EH.

The aqueous decantation phase is removed; the organic phase is returned as flow to the column.

The organic phase has the following composition by mass:

| | |
|---|---|
| Water | 4.1% |
| AA | 16.7% |
| 2-Ethylhexanol | 79% |
| Octenes | 140 ppm. |

EXAMPLE 4

Preparation of 2-ethylhexyl acrylate

Example 3 is repeated, replacing Resin 1 by Resin 2.

The mixture of reactants, AA (containing 500 ppm of 1,1,3-tris(2-methyl-4-hydroxy-5-tert-butylphenyl)butane (TOPANOLO® CA) and 500 ppm of HQ) and E2HOH, is pumped at 90° C. into the first reaction stage 13 at a flow rate of 433 ml/h.

The initial AA/E2HOH molar ratio is 1.25.

The residence time on the resin 13 is 27 min and the temperature at the centre of the bed of resin is 95° C.

The amount of resin, dried in a ventilated oven, employed is 170 g.

The composition by mass at the exit from the cartridge 13 is as follows:

| | |
|---|---|
| E2HOH | 30.3% |
| AA | 24.2% |
| Water | 4.1% |
| A2EH | 37.5% |
| Octenes | 500 ppm |
| Maleic impurities (maleic acid + mono- + dimaleates) (these depend on the quality of the technical-grade AA used) | 1600 ppm |
| 2-Ethylhexyl hydroxypropionate | 1.2% |
| 2-Ethylhexyl acryloyloxy-propionate | 1.3% |
| 2-Ethylhexyl 2-ethylhexyloxy-propionate | 0.2%. |

The degree of conversion of the AA is 48.1%, or 93.8% of the thermodynamic equilibrium.

The crude product exiting the first stage 13 is subsequently pumped to the second stage for post-esterification therein.

The feed flow rate is 190.5 g/h. A complement of E2HOH containing 500 ppm of HQ is added at the top of column 6. The overall (first+second stage) AA/E2HOH molar ratio is 0.8/1. A gentle bubbling of air is carried out in the blending tank 1. The temperature inside the tank 1 is 107° C. The temperature at the top of column 6 is 38° C. at the pressure of 6.66×10³ pa (50 mmHg).

The crude product at the exit 1 is recirculated at a flow rate of 20.6 l/h in the cartridge 9, which is packed with 134 g of dry Resin 2.

The temperature at the centre of the bed of resin 9 is 96° C.

The water of reaction is removed in the form of an azeotrope at the top of column 6.

The vapours are condensed at the top of the column and decanted at ambient temperature.

The aqueous phase is removed; the organic phase is returned as flow to the column.

The crude product at the exit from the second stage has the following composition by mass:

| | |
|---|---|
| E2HOH | 37.4% |
| AA | 10.7% |
| Water | 0.12% |
| A2EH | 47.2% |
| Octenes | 1000 ppm |
| Ethers | 500 ppm |
| Maleic impurities (maleic acid + mono- + dimaleates) | 1600 ppm |
| AA dimer | 1000 ppm |
| 2-Ethylhexyl hydroxypropionate | 1.3% |
| 2-Ethylhexyl acryloyloxy-propionate | 2.3% |
| 2-Ethylhexyl 2-ethylhexyloxy-propionate | 0.8%. |

The degree of conversion of the AA is 67%.

The preceding examples can be repeated with similar success by substituting the generically or specifically described reactants and/or operating conditions of this invention for those used in the preceding examples.

The entire disclosure of all applications, patents and publications, cited above, and of corresponding French application 0017023 filed Dec. 26, 2000, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process for preparing an unsaturated carboxylic ester by esterifying an unsaturated carboxylic acid reactant with an alcohol reactant in the presence of a cationic resin catalyst, the water of reaction being removed in the form of an azeotrope with the esterifying alcohol or with a solvent, the improvement comprising passing a mixture of reactants in an upflow mode through a bed (9) of the said cationic resin withdrawing resultant reaction mixture from the top of the bed (9) and passing said resultant reaction mixture to a stirred tank (1) and blending the resultant reaction mixture with reactants which have not traversed said bed (9), and recirculating a portion of the resultant blend up through the bed (9) and into the stirred tank (1) though a recirculation route (2).

2. Process according to claim 1, characterized in that a partial reaction is conducted upstream of the stirred tank (1) by passing the mixture of reactants in upflow mode through a second bed (13) of the cationic resin catalyst.

3. A process according to claim 1, wherein the unsaturated carboxylic acid is acrylic or methacrylic acid.

4. A process according to claim 3, wherein the alcohol is a primary or secondary $C_1$-$C_{12}$ aliphatic alcohol.

5. Process according to claim 4, characterized in that the alcohol is selected from n-butanol, 2-ethylhexanol and n-octanol.

6. A process according to claim 1, wherein the overall unsaturated carboxylic acid/alcohol molar ratio is between 0.6 and 1.

7. A process according to claim 1, wherein the reaction is conducted in the presence of at least one polymerization inhibitor selected from phenothiazine, hydroquinone, hydroquinone monomethyl ether, and sterically hindered phenols, at levels in the medium of between 500 to 5 000 ppm.

8. Process according to claim 7, characterized in that the polymerization inhibitor or inhibitors is or are introduced with the reactants at the top of the distillation column (6) surmounting the stirred tank (1).

9. A process according to claim 1, wherein a portion of the alcohol is introduced at the top of a distillation column (6) surmounting the stirred tank (1), one or more polymerization inhibitors being advantageously combined with the alcohol introduced at the top of column (6), and the proportion by mass of the alcohol thus introduced at the top of column (6) relative to the alcohol introduced into the tank (1) being from 20 to 60%.

10. A process according to claim 1, wherein the bed of resin (9) exhibits at the top thereof a temperature of between 70 to 100° C., the temperature of the stirred tank (1) is between 100 to 110° C., a reaction mixture exits the stirred tank (1), is cooled at 80–90° C. and is then recirculated through the bed of resin (9).

11. A process according to claim 1, wherein the cationic resin is a strong cationic styrene/divinylbenzene resin containing sulphonic groups, having an ionic capacity of between 0.5 and 2.2 equivalents/liter.

12. A process according to claim 1, wherein the reaction mixture is circulated through the bed of resin (9), the overall residence time on the bed of resin (9) being between 0.5 and 2 h.

13. A process according to claim 1, wherein the working pressure at the top of the distillation column (6) surmounting the stirred tank (1) is from $9.33 \times 10^3$ to $5.3$ to $10^4$ Pa (from 70 to 400 mmHg).

14. A process according to claim 2, wherein the temperature at the top of the second bed (13) is from 80 to 95° C.

15. A process according to claim 2, wherein the second bed (13) is operated at atmospheric pressure under conditions of thermodynamic equilibrium.

16. A process according to claim 2, wherein the residence time on the resin of the second bed (13) is from 20 to 60 minutes.

17. A process according to claim 2, at the second catalytic bed (13), the acid/alcohol molar ratio is top-heavy in acid.

18. A process according to claim 6, wherein the acid/alcohol molar ratio is between 0.7 and 0.9.

19. A process according to claim 9, wherein said proportion is from 30 to 50%.

20. A process according to claim 10, wherein the temperature at the top of the bed of resin (9) is between 80° C. and 95° C.

* * * * *